（12）United States Patent
Sheinman et al.

(10) Patent No.: US 6,241,752 B1
(45) Date of Patent: Jun. 5, 2001

(54) METHOD OF TREATING FOR IMPOTENCE AND APPARATUS PARTICULARLY USEFUL IN SUCH METHOD

(75) Inventors: Shuki Sheinman, Raanana; Abraham Ami Sidi, Ramat Gan; Yacov Yacobi, Kiryat Ono, all of (IL)

(73) Assignee: Inventis, Raanana (IL)

( * ) Notice: Subject to any disclaimer, the term of this patent is extended or adjusted under 35 U.S.C. 154(b) by 0 days.

(21) Appl. No.: 09/128,541

(22) Filed: Aug. 4, 1998

Related U.S. Application Data

(60) Provisional application No. 60/084,747, filed on May 8, 1998.

(51) Int. Cl.$^7$ .................................................. A61N 5/006
(52) U.S. Cl. .................................. 607/91; 606/16; 607/89
(58) Field of Search ............................ 607/91–97, 138, 607/154, 143; 606/10, 15, 16; 128/288

(56) References Cited

U.S. PATENT DOCUMENTS

| | | |
|---|---|---|
| 4,633,870 | 1/1987 | Sauer . |
| 4,951,663 | 8/1990 | L'Esperance, Jr. . |
| 5,199,442 * | 4/1993 | Seager et al. ......................... 128/788 |
| 5,366,490 * | 11/1994 | Edwards et al. ....................... 607/99 |
| 5,478,339 * | 12/1995 | Tadir et al. ............................ 606/15 |
| 5,500,918 * | 3/1996 | Pileski et al. ........................ 385/117 |
| 5,571,118 * | 11/1996 | Boutos ................................. 607/138 |
| 5,649,972 | 7/1997 | Hochstein . |
| 5,692,520 * | 12/1997 | Lavoisier ............................. 128/774 |
| 5,968,033 * | 10/1999 | Fuller et al. ............................ 606/9 |

\* cited by examiner

*Primary Examiner*—Michael Peffley
*Assistant Examiner*—Ahmed Farah
(74) *Attorney, Agent, or Firm*—Birch, Stewart, Kolasch & Birch, LLP

(57) ABSTRACT

An apparatus for treating a male for impotence, i.e., for enabling, or improving the ability of, the male to achieve or maintain a penile erection of adequate rigidity for sexual intercourse, by applying monochromatic light radiation, preferably low-power laser radiation of a wavelength of 440 nm, to the penis of the male, sufficient to induce relaxation of the walls of the blood vessels supplying blood to the corpora cavernosa of the penis.

18 Claims, 7 Drawing Sheets

METHOD OF TREATING FOR IMPOTENCE AND APPARATUS PARTICULARLY USEFUL IN SUCH METHOD

This application claims benefit to U.S. provisional application Ser. No. 60/084,747, filed May 8, 1998.

FIELD AND BACKGROUND OF THE INVENTION

The invention relates to a method of treating a male for impotence, namely a male's inability to achieve or maintain a penile erection of adequate rigidity for sexual intercourse. The invention also relates to apparatus for irradiating an object with monochromatic light, preferably a laser beam, which apparatus is particularly useful in such method.

The penis consists of two longitudinal cylindrical bodies called the corpora cavernosa. These bodies are composed of sponge-like tissue that contains tiny vascular spaces (cavernous sinuses) surrounded by smooth muscle. A third cylinder is the urethra, a tube that carries the urine and the ejaculate. Blood flows to the penis via two very small arteries that come from the aorta. During erection, blood is pumped into the penis under great pressure, and a series of valves trap the blood in the penis to maintain the erection.

The sequence of events that initiate an erection includes relaxation of the sinusoid muscle, which results in a decrease of resistance and an increase in blood flow. The events that lead to this smooth muscle relaxation are controlled by biochemical substances which are released from the nerve endings after sexual stimulation. These substances include, among others, the endothelium-derived relaxing factor (EDRF), also known as nitric oxide (NO). NO has been found to act as a neurotransmitter causing smooth muscle relaxation in the urogenital tract and seems to be the final mediator of penile erection. Penile erection is mediated by nitric oxide via cyclic guanosine monophosphate. Any medication or process which will mimic these mechanisms will enhance an erection.

Following are the main types of impotence and their causes:

psychogenic impotence, caused by impulses from the brain which inhibit the erectile process;

neurogenic impotence, secondary to nervous system disorders;

arteriogenic impotence, secondary to disease of the arteries which supply blood to the penis;

hormonal impotence, caused by a deficiency of androgens and loss of sexual interest and erections;

impotence caused by a deficiency of nitric oxide (NO) production in the corpora cavernosa of the penis, which has been implicated in erectile dysfunction;

venogenic impotence, caused by abnormal venous channels of communication, producing an inability to maintain an erection; and erectile tissue disfunction impotence, secondary to fibrosis, trauma, diabetes, tumor infiltration and others.

Currently the following methods are used in the treatment of impotence i.e., to enable, or to improve the ability of, a male to achieve or maintain a penile erection of adequate rigidity for sexual intercourse:

vacuum constrictor devices; however these may be cumbersome to use and may cause pain and/or premature loss of penile tumescence/rigidity.

transdermal administration of vasoactive drugs; however these are usually ineffective.

transurethal administration of vasoactive drugs; however these may cause pain and insufficient erection.

intracavernous injection of vasoactive agents; however these are frequently accompanied by side effects including hematomas, pain, formation of fibrotic nodules within the corpora cavernosa, penile curvature and priapism.

penile prosthesis implantation; however this involves irreversible destruction of corpora cavernosa vessels, and possible complications including infection, erosion of a component of a prosthesis, and mechanical failure of prosthesis components.

sildenafil (e.g., Viagra, the recently introduced drug) which prevents degradation of the cyclic guanosine monophosphate and thus enhances erections; however, this may be accompanied by serious, possibly fatal, side effects.

OBJECTS AND SUMMARY OF THE PRESENT INVENTION

An object of the present invention is to provide a novel method of treating a male for impotence, i.e., for enabling, or improving the ability of, the male to achieve penile erection of adequate rigidity for sexual intercourse, which method has advantages in one or more of the above respects. Another object of the invention is to provide apparatus for irradiating an object with light radiation, preferably laser radiation, which apparatus is particularly useful in the above method but could conceivably be used in other applications.

According to one broad aspect of the present invention, therefore, there is provided a method of treating a male for impotence, comprising: applying low-power monochromatic light radiation to the penis of the male sufficient to induce relaxation of the walls of the blood vessels supplying blood to the corpora cavernosa of the penis.

According to further features in the preferred embodiment of the invention described below, the monochromatic light radiation is laser radiation of a wavelength of 440–960 nm, and is applied at a rate (irradiance) of 20–2000 millewatts per square centimeter for a total energy (radiant exposure) of 50–200 joule per square centimeter for a treatment time of 1.5–40 minutes.

According to still further features in the described preferred embodiments, the radiation is applied while it is moved along the length of the penis. Preferably, the radiation is applied through one or more cycles, each including a slow forward stroke having a duration in the order of minutes, and a quick return stroke having a duration in the order of seconds.

It is believed that the foregoing method can be used for treating a male for impotence without the side effects and other drawbacks present in the currently used methods.

Thus, recent studies have shown that monochromatic light radiation, particularly laser radiation, induces relaxation of vascular smooth muscle in vitro and in vivo at low powers. At high power, predominantly heat formation, constriction, focal coaguli formation, hemostasis and thermal damage to tissues occur. The shorter is the light wavelengths, the more effective is the relaxation.

In addition, low-power monochromatic, preferably laser, radiation has been reported to reduce injury, to promote regenerization, to provide protective effects against ischemic damage, and to produce analgesia. While the mechanism is unknown, one hypothesis is that the radiation produces free radicals (EDRF), like nitric oxide (NO), which have beneficial effects on impotence at low concentrations. Suggested causes of blood vessel wall relaxation by laser or other monochromatic light are similar to the endothelium-derived relaxation (based on endothelium-derived relaxing factor, EDRF) and depends on the presence of nitric oxide (NO) donors.

However, the exposure to the laser radiation should be within the exposure limits set forth in the Guidelines of the International Commission On Non-Ionising Radiation Protection (ICNIRP), e.g., as published in the Eighth International Congress Of The International Radiation Protection Association, Montreal, May 18–22 1992.

According to another aspect of the present invention, there is provided apparatus for treating a male for impotence, comprising: a source of low-power, monochromatic light radiation; and a radiation applicator for holding the male's penis and for applying to a large surface area thereof monochromatic light radiation from the source sufficient to induce relaxation of the walls of the blood vessels supplying blood to the corpora cavernosa of the penis.

According to a further aspect of the invention, there is provided apparatus for treating a male for impotence, comprising: a source of low-power, monochromatic light radiation; and a radiation applicator for holding the male's penis and for applying to a large surface area thereof monochromatic radiation from the source sufficient to improve the male's ability to achieve and maintain penile erection as a result of a sexual stimulation.

According to yet another aspect of the present invention, there is provided apparatus for irradiating an object with light radiation, which apparatus is particularly, but not exclusively, useful in the above method. The novel apparatus comprises: a radiation source outputting a radiation beam; a radiation applicator including an object supporting device for supporting the object to be irradiated; a radiation guiding conduit guiding the radiation beam from the light source to the radiation applicator; the radiation guiding conduit including a plurality of optical fibers having inlet ends for receiving the radiation beam from the light source, and outlet ends distributed along the surface of the object to be irradiated for irradiating the surface; and a radiation distributor between the light source and the inlet ends of the optical fibers for sweeping the radiation beam across the inlet ends of the optical fibers and thereby for distributing the radiation beam across the surface of the object to be irradiated.

According to further features in the described preferred embodiment, the outlet ends of the optical fibers are arrayed in a matrix extending axially and transversely of the object to be irradiated. The inlet ends of the optical fibers are arrayed in a cylindrical matrix extending axially and transversely of the radiation distributor; and the radiation distributor distributes the radiation beam with respect to the inlet ends of the optical fibers.

In one described embodiment, the radiation distributor includes a mirror which is rotated by a rotary drive and is moved axially by an axial drive to sequentially sweep the radiation beam across the inlet ends of the optical fibers. In a second described embodiment, the radiation distributor includes a beam expander for expanding the radiation beam outputted by the light source; a conical deflector for deflecting the radiation beam laterally towards the inlet ends of the optical fibers; and an axial drive for driving the conical deflector axially with respect to the inlet ends of the optical fibers. In a third described embodiment, the radiation distributor includes a plurality of light modulators axially-aligned with the light source, and axially-spaced from each other, for distributing the radiation beam with respect to the inlet ends of the optical fibers.

According to still further features in the described preferred embodiments, the radiation applicator includes a cavity for receiving the object, the radiation applicator being formed with a plurality of openings arrayed both circumferentially and axially of the cavity and fixedly receiving the outlet ends of the optical fibers. More particularly, where the apparatus is to be used for treating for impotence, the light source is preferably a laser outputting a low-power leaser beam of 440–960 nm; the radiation applicator is made of resilient material; and the semi-cylindrical cavity is configured to receive the penis of a male to be irradiated with the laser radiation.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

The apparatus illustrated in FIGS. 1–5 of the drawings is particularly useful for treating a male for impotence by applying low-power monochromatic light radiation, preferably laser radiation, to the penis of the male sufficient to induce relaxation of the walls of the blood vessels supplying blood to the corpora cavernosa of the penis. The manner in which the illustrated apparatus is used is described below following the description of the structure of the apparatus.

Figure 1:
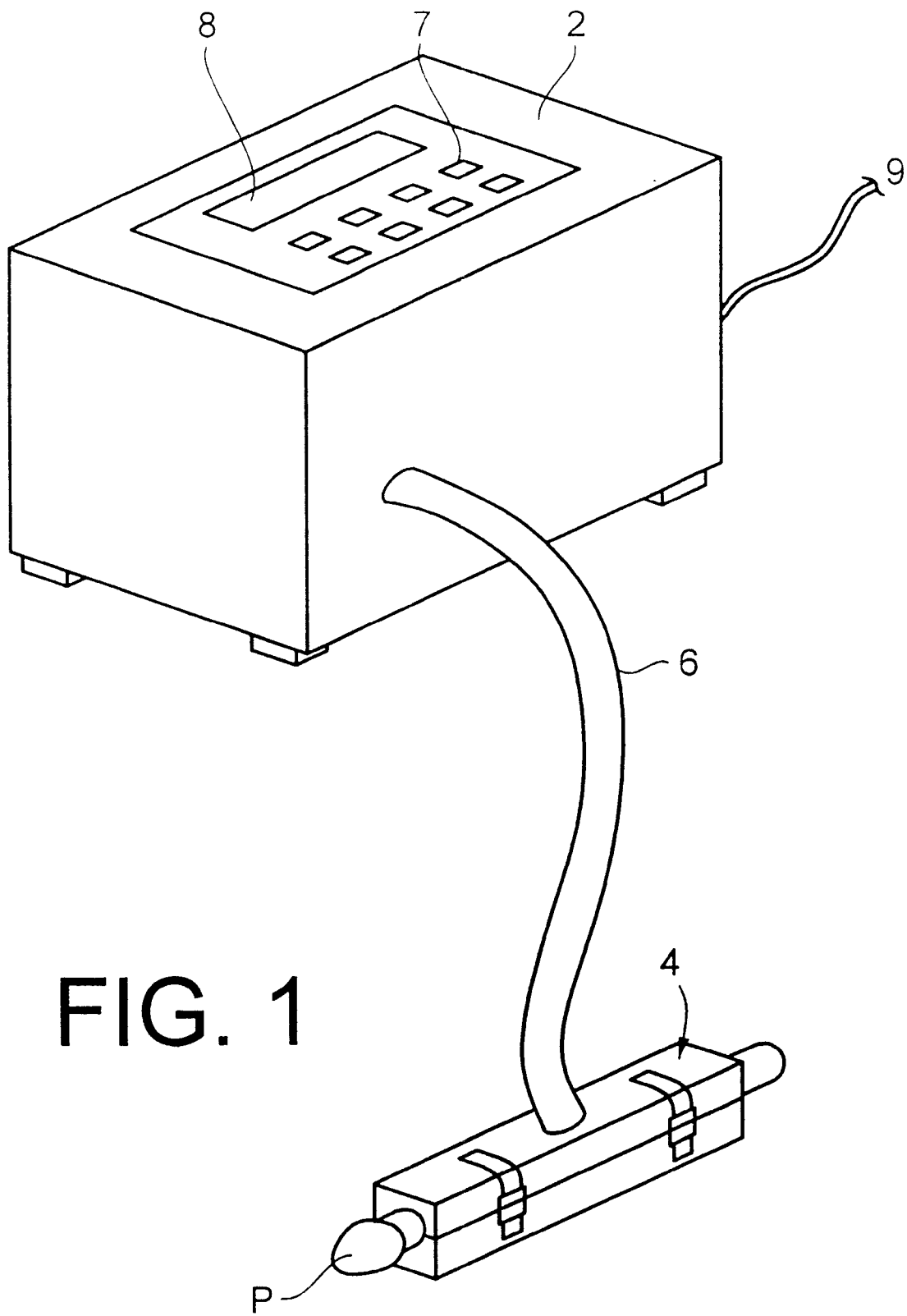
FIG. 1 illustrates one form of apparatus constructed in accordance with the present invention.

FIG. 1 illustrates the overall apparatus. The apparatus includes a housing, generally designated 2, which houses a monochromatic light source, preferably a laser, and a radiation distributor as will be described more particularly below with respect to FIGS. 2–5; a radiation applicator, generally designated 4, for applying the radiation to the male's penis shown at P; and a radiation guiding conduit, generally designated 6, guiding the radiation from housing 2 to the applicator 4. Housing 2 further includes a programming panel 7 enabling the illustrated apparatus to be programmed as will be described more particularly below, and a display panel 8 displaying information regarding the operation of the apparatus.

Electrical power to the radiation source and the radiation distributor within housing 2 is supplied by a cable 9.

Figure 2:
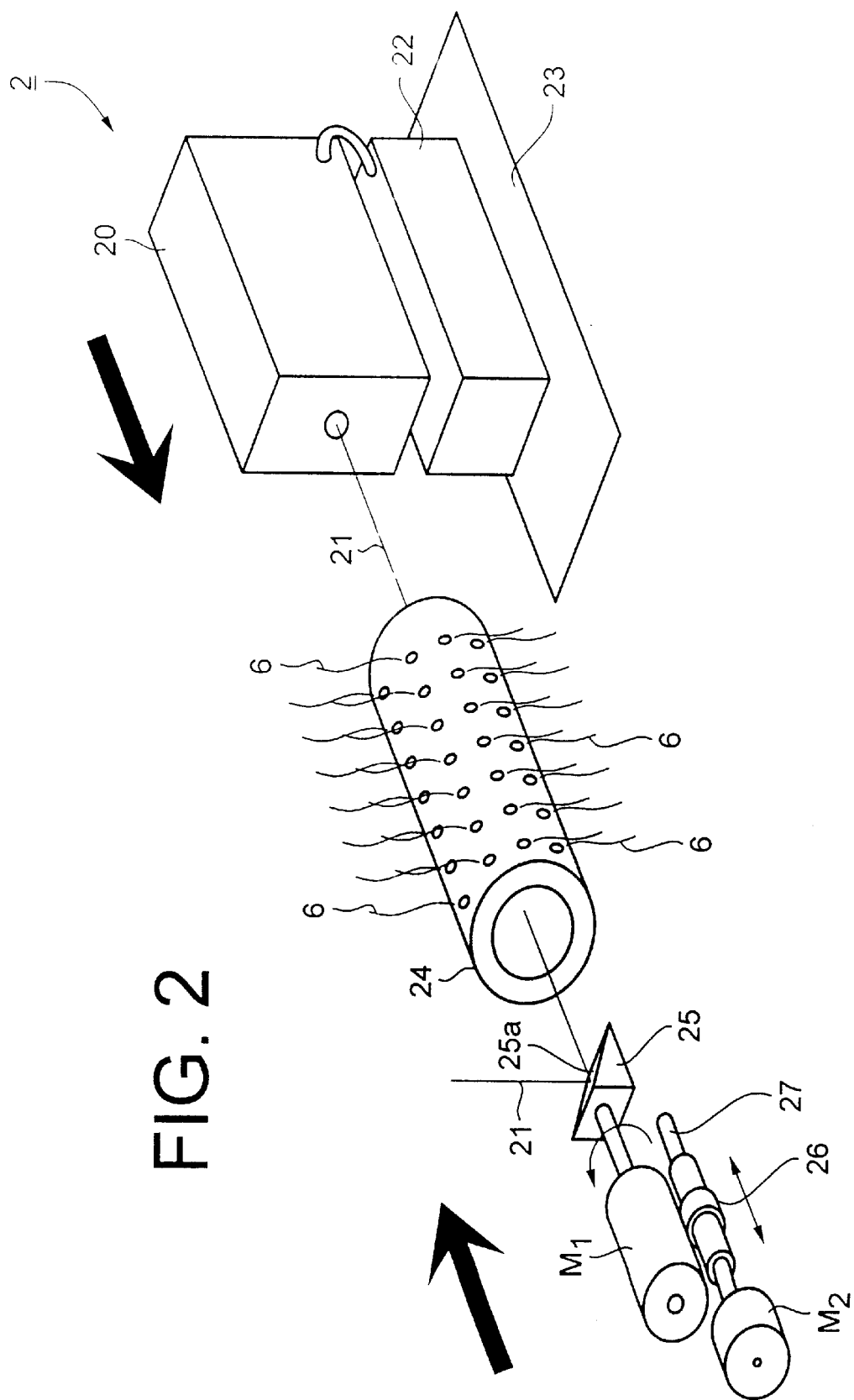
FIG. 2 illustrates a rotating-mirror type of radiation distributor in the apparatus of FIG. 1.
Figure 3:
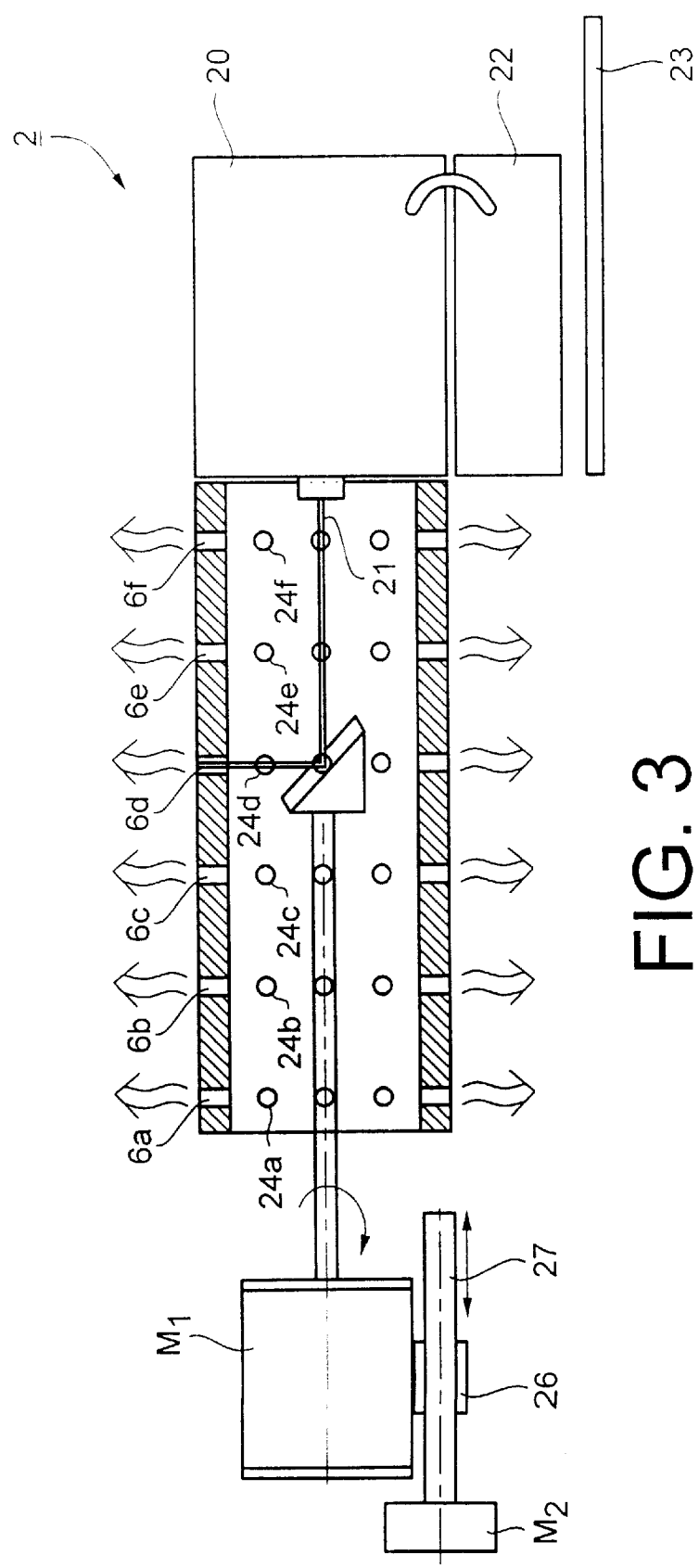
FIG. 3 is a longitudinal sectional view of the radiation distributor of FIG. 2.

FIGS. 2 and 3 illustrate the monochromatic light source, and also the radiation distributor, within housing 2. Thus, as shown in FIGS. 2 and 3, housing 2 includes a laser 20 (or other monochromatic light source) outputting a laser (or other monochromatic light) beam 21, a power supply 22 for laser 20, and a control board 23 for controlling the energization of the laser.

The radiation distributor within housing 2 includes a cylindrical tube 24 formed with a plurality of openings 24a, each receiving the inlet end of an optical fiber in the radiation guiding conduit 6, and a mirror 25 which is moved both rotatably and axially for sweeping the laser beam 21 successively across the inlet ends of the optical fibers 6. Thus, distributor tube 24 is coaxial with the laser beam 21; and mirror 25 is movable, both rotatably and axially, within tube 24. Mirror 25 includes a 45-degree face to the laser beam 21 so that as the mirror is rotated, it deflects the beam around the inner circumference of tube 24; and as the mirror is moved axially, it deflects the beam to a different circumferential surface of the tube.

Mirror 25 is driven in the rotary direction by a motor $M_1$, and in the axial direction by a motor $M_2$. Motor $M_1$, directly coupled to mirror 25, is carried on a nut 26 movable along a lead screw 27, rotated by motor $M_2$, such that the rotation of motor $M_2$ moves motor $M_1$, and mirror 25 with it, axially within tube 24.

Preferably, both motors $M_1$ and $M_2$ are step motors, or other intermittently driven motors, for driving mirror 25 in steps. Thus, in the normal operation of the apparatus, motor $M_1$ would be driven in steps in order to successively deflect the laser beam 21 to the inlet ends of the optical fibers 6 around the circumference of tube 24 at one axial position of the mirror; motor $M_2$ would be energized to step the mirror 25 to another axial position; and then motor $M_1$ would again be energized (or would be continuously energized) to deflect the laser beam to the inlet ends of the optical fibers at that axial position of the mirror.

FIG. 3 illustrates six circular arrays 24a–24f of openings in the distributor tube 24, with the inlet ends of the optical fibers 6 fixed within these openings to form six circular arrays 6a–6f of fiber inlet ends. FIG. 3 illustrates mirror 25 in the axial position wherein it deflects the laser beam 21 to the circular array of fiber ends 6d, such that energization of motor $M_1$ will cause mirror 25 to deflect the laser beam 21 successively to each of the fiber ends 6d. When the axial motor $M_2$ is energized, this will cause mirror 25 to become aligned with a different circular series of fiber ends, according to the direction end amplitude of this axial movement of the mirror.

It will thus be seen that the inlet ends of the optical fibers received within the openings of the distributor tube 24 are arranged in a matrix extending axially and transversely of the distributor tube. It will also be seen that by controlling rotary motor $M_1$ and axial motor $M_2$, mirror 25 may be moved within distributor tube 24 to sweep the laser beam 21 successively to the inlet ends of all the fibers 6.

Figure 4:
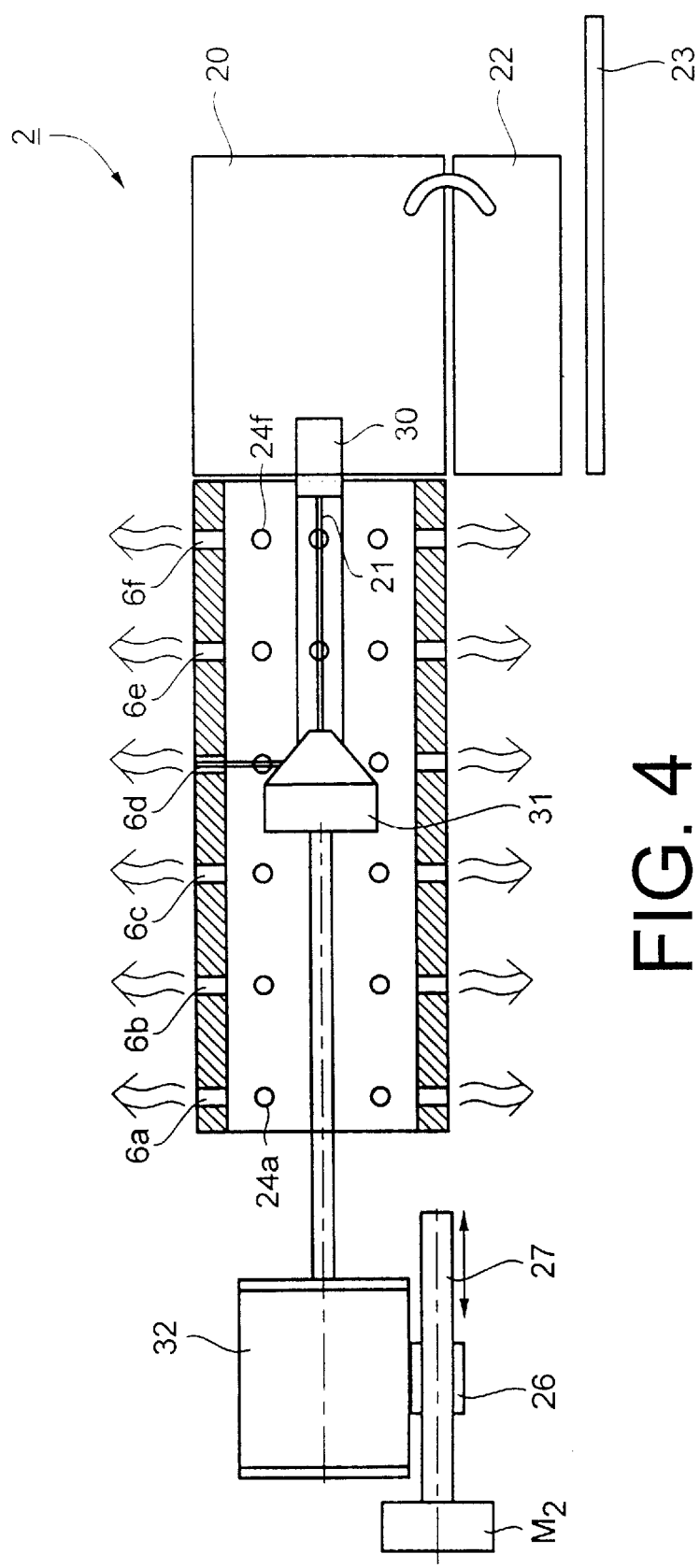
FIG. 4 is a view similar to that of FIG. 3 but illustrating a conical-deflector type of radiation distributor.
Figure 5:
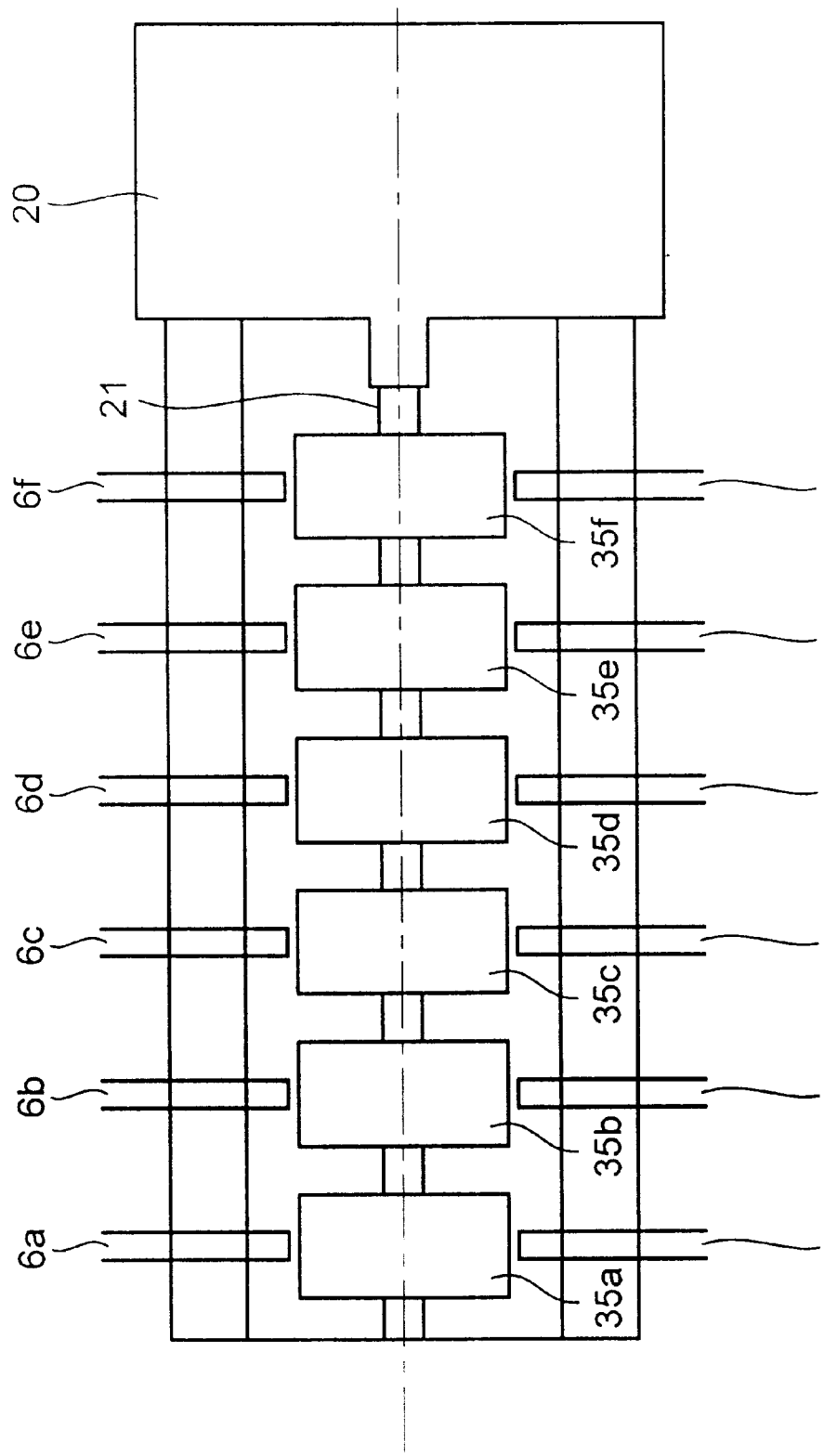
FIG. 5 is a view similar to that of FIG. 3 but illustrating a light-modulator type of radiation distributor.

FIGS. 4 and 5 illustrate two other types of radiation distributors that may be used instead of the rotating-mirror of FIG. 3.

In FIG. 4, the radiation distributor includes a beam expander 30 outputting an expanded beam of parallel arrays to a conical deflector 31, e.g., a conical mirror, which deflects the expanded beam laterally towards the outlet ends of the optical fibers 6a–6f. Thus, the conical deflector 31 needs to be driven only in the axial direction, this being done by motor $M_2$, to sequentially sweep the laser radiation from the conical deflector 31 across the six circular arrays 6a–6f of the fiber inlet ends. The arrangement illustrated in FIG. 4 thus obviates the need of motor $M_1$ for rotating the laser beam about the beam axis from the laser, and therefore motor $M_1$ of FIG. 3 is replaced merely by a head 32 supporting the conical deflector 31 and moved axially by motor $M_2$.

FIG. 5 illustrates a radiation distributor which includes a plurality of light modulators 35a–35f axially-aligned with the laser axis, and axially-spaced from each other, for distributing the laser beam with respect to the inlet ends 6a–6f of the optical fibers. Light modulators 35a–35f may be in-line modulars to produce an axial sweep of the laser beam with respect to the fiber ends, or matrix modulators to produce also a rotary sweep of the laser beam with respect to the fiber ends. The arrangement illustrated in FIG. 5 thus obviates the need for both motors $M_1$ and $M_2$ in the rotary flat-mirror distributor illustrated in FIG. 3.

The optical fibers 6 in all the above-described arrangements guide the laser radiation from housing 2 to the radiation applicator 4 to distribute the radiation over the surface of the penis P within the radiation applicator.

Figure 6:
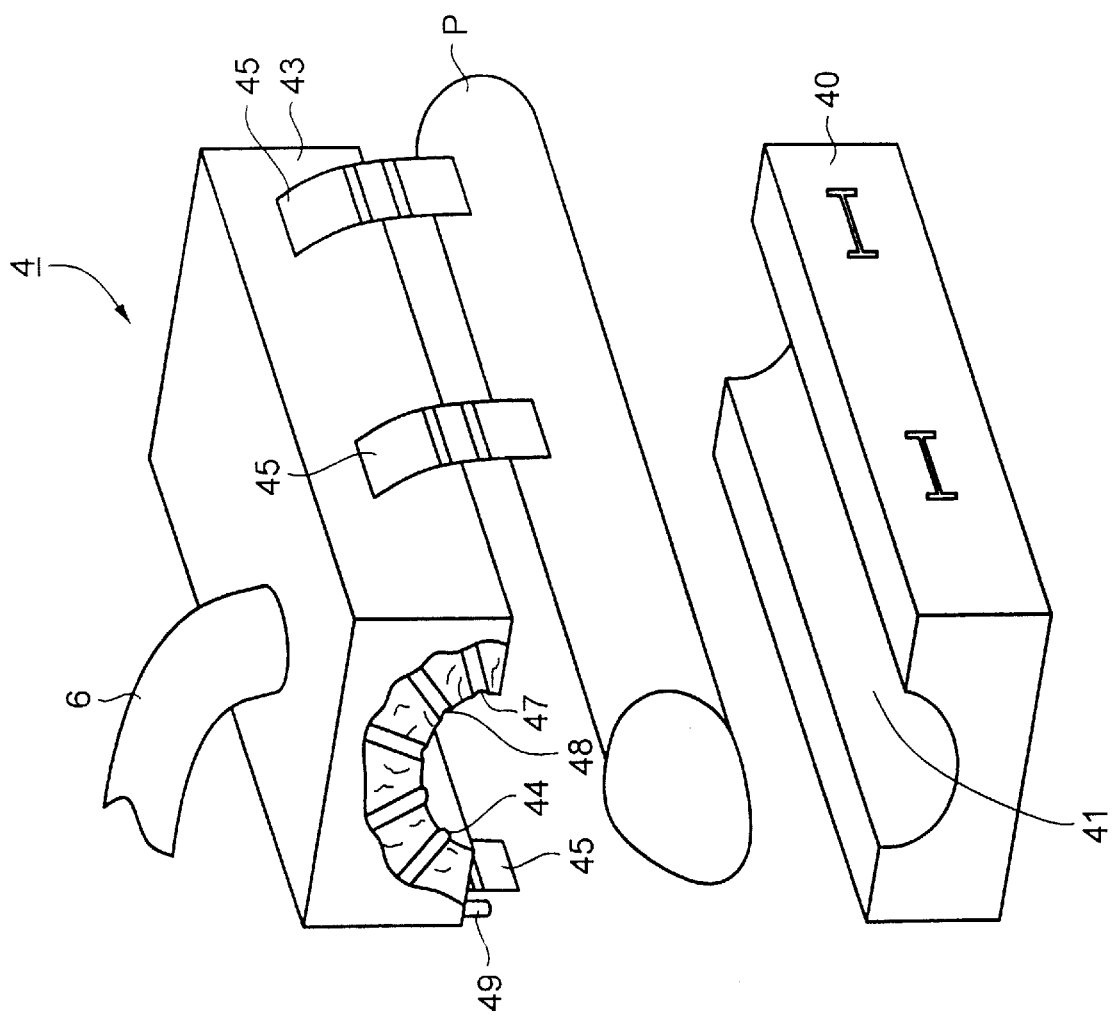
FIG. 6 is an exploded view illustrating the radiation applicator in the apparatus of FIG. 1.
Figure 7:
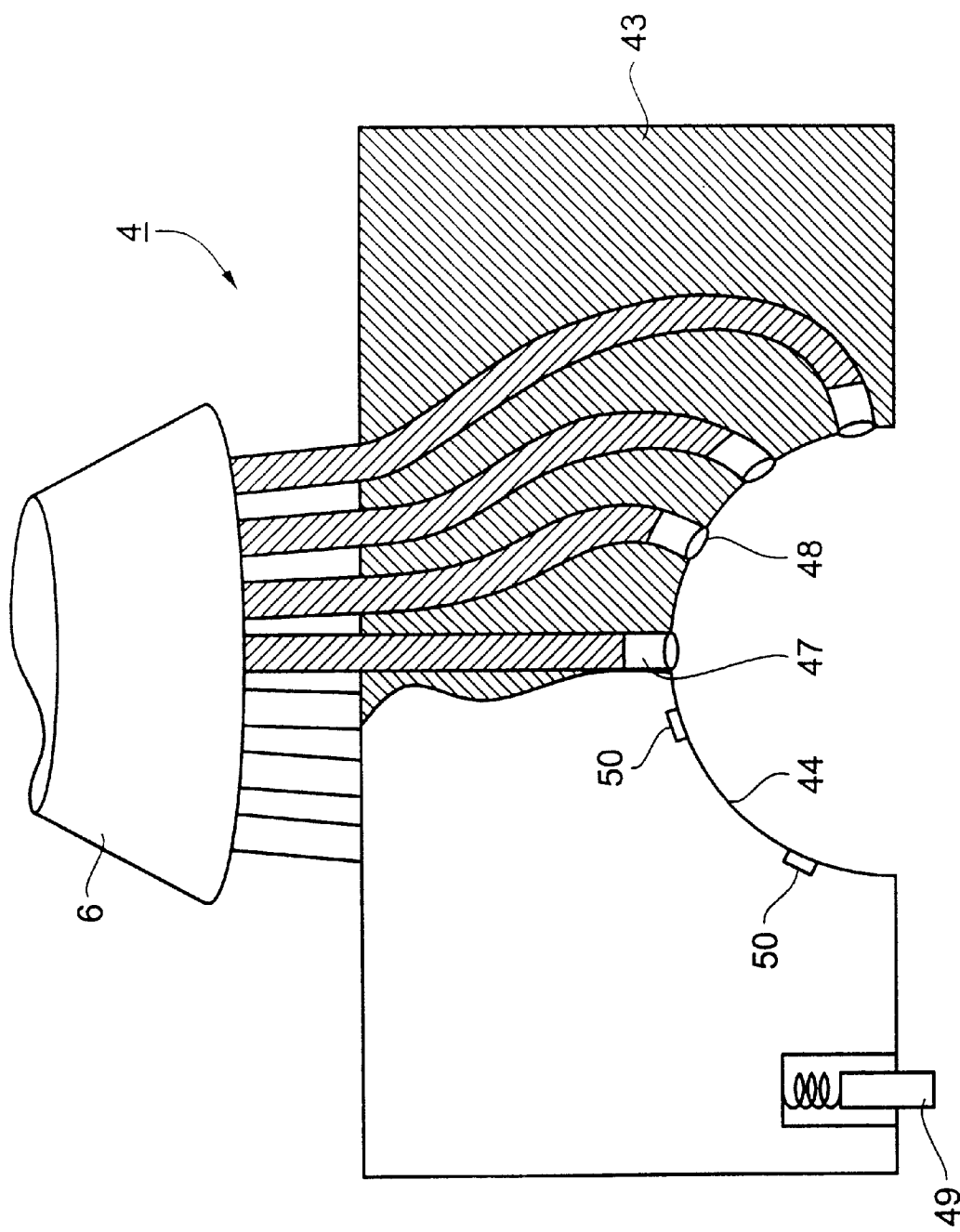
FIG. 7 is a view, partly broken away, more particularly illustrating the structure of the radiation applicator of FIG. 6.

Thus, as shown in FIGS. 6 and 7, the radiation applicator 4 includes a supporting plate 40 formed with a semi-cylindrical groove 41 to receive the lower half of the penis P, and with an upper plate 43 similarly formed with a semi-cylindrical recess 44 for engagement with the upper part of the penis. The two plates may be clamped together, e.g., by straps 45, to define a cylindrical cavity for receiving the penis. The upper plate 43 is formed with a plurality of openings or passageways 47 for receiving the outlet ends of the optical fibers 6.

The outlet ends of the optical fibers 6 fixed within openings 47 of the radiation applicator 4 are thus also arrayed in a matrix extending axially and transversely of the applicator. In radiation applicator, however, the outlet ends of the optical fibers are arrayed in a semi-cylindrical pattern, rather than in a cylindrical pattern as in the distributor tube 24 receiving the inlet ends of the optical fibers. This is because the radiation is applied only to the upper half of the penis P, proximal to the two corpora cavernosa bodies of the penis.

The radiation applicator 4 further includes a transparent convex lens 48 at the outlet end of each optical fiber 6. Each lens 48, (e.g., spherical or convex-convex) converges the laser radiation applied by its respective optical fiber 6, and also provides a smoother surface for contact with the penis.

Preferably, the upper part 43 of the radiation applicator 4 should be made of a somewhat resilient material, such as silicon rubber, for comfort purposes. The lower part 40 may be made of the same material, or conceivably could even be omitted.

In order to reduce radiation hazards, particularly when a laser is used as the monochromatic light source, the applicator illustrated in FIGS. 6 and 7 is provided with an interlock switch, schematically shown at 49, which must be closed, by the clamping of plate 43 to plate 40, to enable energization of the light source. Thus, whenever the two plates are not clamped together, the light source (e.g., laser) is disabled in order to minimize possible eye or other hazards.

In addition, the surfaces of one or both plates 43, 40, comming into direct contact with the object being irradiated, includes temperature sensors, shown at 50 in FIG. 7. Such sensors will also automatically disable the laser (or other light source) upon the temperature of the irradiation surface exceeding a predetermined value, e.g., by more than 2–3 degrees C. from its normal value.

When the illustrated apparatus is used in treating for impotence, the monochromatic light source 20 is preferably a laser having a wavelength of 440–960 nm. A preferred laser is a helium-neon one having a wavelength of 632 nm, since such lasers are today readily available at relatively low cost. Other lasers that may be used are the helium-cadmium laser having a wavelength of 440 nm, and the diode laser having a wavelength of 780 nm. However, other monochromatic light sources may be used, such as an Xenon lamp with an appropriate collimator, filter, and converging lense.

Preferably, the light radiation is applied at a rate (irradiance) of 20–2,000 millewatts per square centimeter, for a total radiance exposure of 50–200 joules per square centimeter and for a total treatment time of 1.5–40 minutes. For example, when using the helium-neon laser of 632 nm, a preferred irradiance is 100 millewatts per square centimeter, and the preferred treatment time is approximately 2 minutes.

The light radiation is preferably applied in one or more cycles, wherein in each cycle the light radiation is moved slowly through a forward stroke along the penis from one end to the other, and then through a fast return stroke back to its original position. This cyclical movement of the radiation is effected by the radiation distributor, e.g., as illustrated in FIGS. 3, 4 or 5 within distributor tube 24, as described above, to sweep the laser beam 21 successively across each circular series of fiber ends 6a–6f in the distributor tube 24. Each forward stroke preferably has a duration in the order of minutes, and each return stroke preferably has a duration in the order of seconds. As one example, a treatment may include four such cycles, in which each forward stroke is about 5 minutes, and each return stroke is about 6–12 seconds, thereby providing a total treatment time of about 2 minutes.

Preferably, the bundle of optical fibers 6 should include from 40 to 150 optical fibers, all enclosed within a jacket sufficiently stiff to avoid sharp bends in the fibers. As one example, there could be 49 fibers arranged in a 7×7 matrix; and as another example there could be 120 fibers arranged in an 8×15 matrix. Each fiber 6 is preferably from 1–2.5 mm in diameter.

In the FIG. 3 radiation distributor, motor $M_1$ is preferably a stepper motor, operated at 3 RPM, and motor $M_2$ is preferably a stepper motor operated to produce a dwell time for each fiber of 4–8 seconds, but no more than 10 seconds. The radiation distributors illustrated in FIGS. 4 and 5 could be correspondingly operated. Distributor tube 24 is preferably of aluminum, blackened on both surfaces, having an inner diameter of 25 mm, an outer diameter of 50 mm, a thickness of 12.5 mm, and a length of 65–85 mm.

While the invention has been described with respect to several preferred embodiments, it will be appreciated that this is set forth merely for purposes of example, and that many other variations, modifications and applications of the invention may be made.

What is claimed is:

1. Apparatus for treating a male for impotence, comprising:
    a source of low-power, monochromatic light radiation;
    and a radiation applicator for applying to the penis monochromatic light radiation from said source sufficient to induce relaxation of the walls of the blood vessels supplying blood to the corpora cavernosa of the penis.

2. Apparatus for treating a male for impotence, comprising; a source of low-power, monochromatic light radiation, and a radiation applicator for applying to the penis monochromatic radiation from said source in a quantity and over a surface area of the penis sufficient to improve the male's ability to achieve and maintain penile erection as a result of a sexual stimulation.

3. The apparatus according to claim 2, wherein said source of monochromatic light radiation is a laser producing laser radiation of a wavelength of 440–960 nm.

4. The apparatus according to claim 2, wherein the irradiance of said laser is 20–2000 millewatts per square centimeter and is applied for a total radiance exposure of 50–200 joule per square centimeter in a total treatment time of 2–40 minutes.

5. The apparatus according to claim 2, wherein said radiation applicator applies radiation to a portion of the penis, and the location of said portion is slowly moved along the length of the penis.

6. The apparatus according to claim 5, wherein said radiation applicator is coupled to said radiation source by a distributor which moves the location at which the radiation is applied, relative to the penis, to produce at least one radiation exposure cycle including a forward stroke in one direction along the penis and a return stroke in the opposite direction.

7. The apparatus according to claim 6, wherein said forward stroke has a duration in the order of minutes, and said return stroke has a duration in the order of seconds.

8. The apparatus according to claim 2, further comprising a distributor that applies the radiation to the upper part of the penis.

9. The apparatus according to claim 6, wherein s aid applicator includes a holder for holding the penis, and a plurality of optical fibers having inlet ends exposed to said distributor and outlet ends arrayed along the length of said holder.

10. The apparatus according to claim 9, wherein said radiation distributor includes a plurality of light modulators axially-aligned with said radiation source, and axially-spaced from each other, for distributing the radiation beam with respect to said inlet ends of the optical fibers.

11. The apparatus according to claim 9, wherein said holder includes a plate, and said outlet ends of the optical fibers are fixed in said plate.

12. The apparatus according to claim 9, wherein a convex lens is provided at the outlet end of each optical fiber to converge the radiation beam emitted therefrom.

13. Apparatus for irradiating an object with light radiation, comprising:
    a radiation source outputting a radiation beam;
    a radiation applicator including a holder for holding the object to be irradiated;
    a radiation guiding conduit guiding the radiation beam from the light source to the radiation applicator; said radiation guiding conduit including a plurality of optical fibers having inlet ends for receiving the radiation beam from said radiation source, and outlet ends distributed along the length of said holder;
    and a radiation distributor between said radiation source and said inlet ends of the optical fibers for sweeping said radiation beam across said inlet ends of the optical fibers and thereby for distributing the radiation beam along the length of the holder and the object held thereby.

14. The apparatus according to claim 13, wherein said outlet ends of the optical fibers are arrayed in a matrix extending axially and transversely of said holder.

15. The apparatus according to claim 13, wherein said inlet ends of the optical fibers are arrayed in a matrix extending axially and transversely of said radiation distributor; and said radiation distributor distributes said radiation beam with respect to said inlet ends of the optical fibers.

16. The apparatus according to claim 13, wherein said radiation distributor includes a cylindrical tube having a plurality of openings therein arrayed both circumferentially and axially of said tube; said inlet ends of the optical fibers being fixed in said openings.

17. The apparatus according to claim 16, wherein said radiation distributor includes a mirror within said cylindrical tube, said mirror being rotated by a rotary drive and moved axially by an axial drive to sequentially sweep said radiation beam across said inlet ends of the optical fibers.

18. The apparatus according to claim 16, wherein said radiation distributor includes: a beam expander for expanding the radiation beam outputted by said radiation source; a conical deflector within said cylindrical tube for deflecting the radiation beam laterally towards said inlet ends of the optical fibers; and an axial drive for driving said conical deflector axially with respect to said inlet ends of the optical fibers.

* * * * *

UNITED STATES PATENT AND TRADEMARK OFFICE
CERTIFICATE OF CORRECTION

PATENT NO.         : 6,241,752 B1                                         Page 1 of 1
APPLICATION NO.    : 09/128541
DATED              : June 5, 2001
INVENTOR(S)        : Shuki Sheinman et al.

It is certified that error appears in the above-identified patent and that said Letters Patent is hereby corrected as shown below:

At column 10, at line 11 please add the following claims:

-- 19. The apparatus according to claim 6, wherein the forward stroke has a duration of about 5 minutes and the return stroke has a duration of about 6-12 seconds.

20. The apparatus according to claim 8, wherein the distributor applies the radiation to the upper circumferential portion of the penis.

21. The apparatus according to claim 6, wherein the distributor applies the radiation along the upper part of the penis.

22. The apparatus according to claim 21, wherein the distributor applies the radiation along a substantial portion of the length of the upper part of the penis.

23. The apparatus according to claim 21, wherein the distributor applies the radiation to the upper circumferential portion of the penis.

24. The apparatus according to claim 23, wherein the distributor applies the radiation along a substantial portion of the length of the upper circumferential portion of the penis. --

Signed and Sealed this

Fourth Day of March, 2008

JON W. DUDAS
*Director of the United States Patent and Trademark Office*